United States Patent [19]

Honda et al.

[11] Patent Number: 4,970,072
[45] Date of Patent: Nov. 13, 1990

[54] BATH PREPARATION

[75] Inventors: Tsuneo Honda; Toru Asakoshi, both of Tokyo; Hiroshi Ishido, Saitama, all of Japan

[73] Assignees: Chugai Seiyaku Kabushiki Kaisha; Kyodo Milk Industry Corporation Ltd., both of Tokyo, Japan

[21] Appl. No.: 148,120

[22] Filed: Jan. 19, 1988

[30] Foreign Application Priority Data

Jan. 20, 1987 [JP] Japan ................................. 62-10203

[51] Int. Cl.$^5$ ............................................ A61K 35/20
[52] U.S. Cl. ..................................... 424/535; 530/833
[58] Field of Search ......................... 424/95, 401, 535; 530/833

[56] References Cited

U.S. PATENT DOCUMENTS 4,851,235  7/1989  Schwartz et al. ................... 435/255

OTHER PUBLICATIONS

Koehler, cited in Chem. Abstracts, vol. 75 (1971), 25244u.
Sauté, in Cosmetics: Science and Technology, Second Ed., vol. 2, 1972, pp. 505–506.
Obata et al., cited in Chem. Abstracts, vol. 104 (1986), 128654z.
Soviet Inventions Illustrated, Section Chemical, week 8819, May 12, 1988, Derwent Publications Ltd., GB, Abstract No. D21E16 & Su-A-1 342 503 (Cement Ind. Res. Inst.), (UMEA), 07-10-1987.

*Primary Examiner*—Jacqueline Stone
*Attorney, Agent, or Firm*—Browdy and Neimark

[57]  ABSTRACT

A novel bath preparation which comprises a whey concentrate of high mineral content and, if necessary, one or more additives commonly used for conventional bath preparations such as inorganic salts, inorganic acid, organic acid, medicinal herbs, fats and oils, dyestuffs, perfumes, alcohols, and polyhydric alcohols.

The preparation has the great potential to serve as a curative in the treatment of various disease such as shoulder stiffness, neuralgia, lumbago, rheumatism, etc. It also contributes to beautification.

4 Claims, No Drawings

BATH PREPARATION

BACKGROUND OF THE INVENTION

The present invention relates to a novel bath preparation. More particularly, the present invention relates to a bath preparation that contains as an effective ingredient a whey concentrate of high mineral content and which has good health promoting and beautifying effects.

With the growing interest in health and beauty amongst the public at large, a variety of bath preparations specifically oriented to satisfying these concerns have been developed.

Conventional bath preparations contain a variety of active ingredients depending upon the specific objective of their use, including: inorganic salts such as sodium chloride, sodium hydrogencarbonate, sodium carbonate, sodium phosphate, calcium oxide and magnesium carbonate; inorganic acids such as boric acid and silicic anhydride; organic acids such as benzoic acid, citric acid and succinic acid; medicinal herbs such as fennel (*Foeniculi fructus*), phellodendron bark (*Pheiodendri cortex*), Japanese Angelica root (*Angelicae radix*) and cinnamon bark (*Cinnamomi cortex*); together with common additives such as a variety of natural essential oils, dyestuffs, perfumes, fats and oils, and alcohols. The mode of action of such bath preparations and the advantages they bring about depend upon the ingredients incorporated. The following are notable examples: they warm the human body and simulate blood circulation, thereby accelerating the flow of blood in peripheral vessels so as to produce enhanced metabolism; they promote perspiration to help the body excrete effete material; salts are deposited on the body surface during bathing and the resulting film covers the skin to keep the body warm for a long time after bathing, serving as a heat insulator. Aside from these effects, bath preparations are said to have some ability to clean and sterilize the skin, together with curative effects for a variety of dermal and other diseases such as rheumatism and neuralgia, and skin moisturizing effects. Furthermore, bath preparations are even claimed to provide some psychological effects which can have a favourable influence on psychosomatic diseases by virtue of their colors and flavors.

It is also known that some people in Europe have traditionally added cow's milk to baths to exploit its beautifying and health-promoting effects, while other have added whey in expectation of its curative effects with respect to neuralgia and rheumatism.

A prior art technique related to milk-treated baths is a bath preparation in which a dairy ingredient selected from among cow's milk, milk components, powdered milk, unsweetened condensed milk, unsweetened condensed milk components, cream, and cream components is coated with cyclodextrin so as to improve the storage stability of the dairy ingredient (Unexamined Published Japanese Patent Application No. 181013/1985).

An improvement directed to providing better warming and beautifying effects than those attained by natural mineral springs has been proposed (Japanese Patent Publication No. 5382/1978). This is a bath preparation for use in an artificial mineral spring that has improved warming and beautifying effects and which contains a water-soluble salt of sodium or potassium (e.g. sodium carbonate or sodium sesquicarbonate), a chelate-forming water-soluble metal salt present in an amount sufficient to form a chelate through exchange with sodium or potassium bound to skin protein (e.g., a water-soluble salt of an alkaline earth metal such as calcium or magnesium), and a nonionic or anionic surfactant.

The bath preparation proposed in Unexamined Published Japanese Patent Application No. 181013/1985, which contains a coated compound in which a dairy ingredient (e.g., cow's milk, powdered milk or cream) is coated with cyclodextrin, successfully improved the keeping quality of the inherently labile dairy ingredient. However, when this preparation is used in the bath, the cyclodextrin coat dissolves in the bath water and the dairy ingredient becomes directly exposed to the heat of the water, whereupon it deteriorates through accelerated oxidation, causing such troubles as the occurrence of a rancid smell. If one wants to elicit the potentially diverse effects obtainable from the minerals present in cow's milk, considerable amounts of dairy ingredients must be incorporated, but the occurrence of a rancid smell is then accelerated and the bath water becomes very dirty (e.g. cloudiness and formation of a scum ring around the bath).

The bath preparation proposed in Japanese Patent Publication No. 5382/1978 is chiefly intended to provide better warming and beautifying effects by incorporating the two principal ingredients, a water-soluble salt such as sodium carbonate or sodium hydrogencarbonate, and a chelateforming water-soluble salt of an alkaline earth metal such as calcium or magnesium. Therefore, not much can be expected from this bath preparation as regards the curative effects for dermal and other diseases such as rheumatism and neuralgia.

Bathing in milk-treated water has long been considered to be beneficial for beautifying and health-promoting purposes but it has the disadvantage of making the bath water cloudy and leaving a sticky effect on the skin after bathing.

SUMMARY OF THE INVENTION

Under the circumstances described above, the present inventors undertook investigations to develop a new type of bath preparation that is stable, provides health-promoting and beautifying effects and which has curative effects with respect to various diseases. In doing their research work, the present inventors paid special attention to the tradition of bathing in milk-treated water that has long been known to have superior health-promoting and beautifying effects and in whey-treated water that has also been known to have curative effects for neuralgia and rheumatism. The specific objective of the present inventors was to make efficient use of the vitamins and minerals present in these two kinds of bath water.

As a result of their intensive efforts, the present inventors successfully circumvented the problems associated with the prior art techniques and discovered an entirely new type of bath preparation that is stable, displays very good effects in regard to health promotion, beautification and treatment of various diseases, and which yet keeps the bath water clear while also imparting a refreshing effect that remains with the bather after leaving the bath.

An object, therefore, of the present invention is to provide a novel type of clear bath preparation that has a whey concentrate of high mineral content as its active ingredient and which remains stable while exhibiting the intended health-promoting and beautifying effects.

The bath preparation of the present invention is characterized by containing a whey concentrate as the effective ingredient, with one or more known additives for bath preparations being incorporated as required.

DETAILED DESCRIPTION OF THE INVENTION

The whey concentrate used as the effective ingredient in the bath preparation of the present invention has an increased mineral content. It may be prepared by the following procedures.

Skimmed milk obtained by centrifugation of cow's milk, or whey obtained as a by-product in cheese production, is passed through an ultrafiltration membrane so that it is separated into a protein portion and a permeate. Preparation of the whey concentrate starts with the permeate, which is first concentrated under vacuum to increase the solids content to at least about 40%, preferably at least about 60%. Thereafter, the concentrated solution is cooled, for example, to about 20°–30° C., and mixed with ground lactose in an amount of, for example, about 0.01–0.1%. The mixture is continuously cooled with stirring so as to accelerate the crystallization of the lactose. The mixture is cooled to about 7° C. and below and stirred for a period of at least about 2 hours. After the lactose has completely crystallized, it is separated by a suitable technique such as filtration or with a centrifuge, preferably a decantertype centrifuge. The resulting whey solution may be decolored, if necessary, with a suitable decoloring agent such as activated carbon, and subsequently dried by a suitable drying method such as spray drying, so as to produce a whey concentrate in powder form. If a higher mineral content is desired, the whey solution prepared in the first run may be concentrated and subjected to another cycle of lactose crystallization, thereby yielding a whey concentrate having a desired mineral content.

The thus prepared whey concentrate in powder form has a very high mineral content, say, in the range of from about 40% to about 70%. A whey concentrate having such a high mineral content has not been known in the prior art.

The bath preparation of the present invention which contains the above-described whey concentrate as the effective ingredient may incorporate one or more of the common additives as required, such as inorganic salts, inorganic acids, organic acids, medicinal herbs, fats and oils, dyestuffs, perfumes, alcohols, and polyhydric alcohols. Specific examples of such additives are listed below: inorganic salts such as sodium chloride, sodium hydrogencarbonate, sodium carbonate, sodium sulfate, sodium thiosulfate, calcium carbonate, magnesium carbonate, potassium sulfide, potassium bromide, calcium oxide, aluminum sulfate and iron sulfate; inorganic acids such as boric acid, silicic anhydride and metasilicic acid; organic acids such as benzoic acid, citric acid, fumaric acid, tartaric acid and pyrrolidone carboxylic acid; medicinal herbs such as fennel (*Foeniculi fructus*), phellodendron bark (*Pheliodendri cortex*), german chamomile (*Matricaria chamomillae flos*), cinnamon bark (*Cinnamomi cortex*), Japanese Angelica root (*Angelicae radix*), mentha herb (*Menthae herba*), Japanese iris, peony root (*Paeoniae radix*), bitter orange peel (*Aurantii pericaroium*), houttuynia herb (*Houttuvniae herba*), Zanthoxylum fruit (*Zanthoxyli fructus*) and Borneo camphor (borneol); fats and oils such as olive oil, soybean oil, rice bran oil and liquid paraffin; alcohols such as ethanol, stearyl alcohol, isopropyl alcohol and cetyl alcohol; polyhydric alcohols such as glycerin, propylene glycol, sorbitol and polyethylene glycol; known synthetic perfumes; natural perfumes; known dyestuffs; and miscellaneous additives such as sulfur, mineral sand, sodium salicylate, vitamins, egg yoke powder, polyvinylpyrrolidone, and carboxymethyl cellulose sodium.

The additives for bath preparation illustrated above may be selected as appropriate for the specific use of the bath preparation. They may be used in any desired form such as a powder, granules, tablets, paste or, if they are herbs, in the form of an extract or shreds of a suitable size. The amount in which these additives are used also depends on the specific use of the bath preparation.

Depending upon the specific objective of use, the bath preparation of the present invention may be formulated in a desired dosage form such as a powder, granules, a solution or tablets.

The amount in which the whey concentrate is incorporated in the bath preparation of the present invention is in no way limited and can be appropriately selected according to the specific objective of using this bath preparation. As a guide, the whey concentrate may be incorporated in an amount ranging from about 2 to about 80 wt % of the bath preparation.

The method of producing the bath preparation of the present invention depends upon its dosage form (whether of the powder type, granule type, solution type or tablet type) or on the kind and dosage form of the additives described above. Generally, the bath preparation can be readily produced by merely mixing the whey concentrate with one or more of the additives that are illustrated above and which match a specific type of bath preparation. Alternatively, such additives may be formulated in a variety of dosage forms before they are mixed with the whey concentrate to make a specific type of bath preparation.

The bath preparation made according to the present invention has a very high content of milk-derived minerals such as sodium, potassium, calcium and magnesium. Because of such high mineral content, the preparation has the great potential to serve as a curative in the treatment of various diseases such as shoulder stiffness, neuralgia, lumbago, rheumatism, oversensitiveness to cold, chapped hand, frostbite, miliaria, common acne, eczema and athlete's foot. It also contributes to beautification. A further advantage is that unlike milk-treated bath water, the bath preparation of the present invention leaves no stickiness on the skin after bathing and instead will give a highly refreshing effect while keeping the body warm for an extended period of time.

The following referential example and working examples are provided for the purpose of further illustrating the present invention and are by no means intended to be limited.

REFERENTIAL EXAMPLE

Preparation of a whey concentrate (with 50% mineral content)

Skimmed milk (1,000 g) was passed through an ultrafiltration membrane (average pore size, 0.01–0.05 μm) to separate it into a protein portion and a permeate. The permeate was concentrated at 50°–60° C. at 600–700 mmHg to obtain a solids content of ca. 60%. Thereafter, the concentrated solution was cooled to about 25° C. and charged into a tank equipped with a cooler and a stirrer. When the temperature had decreased to about 25° C., ground lactose was added to the concentrated solution in an amount of about 0.1% of that solution and the cooling was continued with stirring to accelerate the crystallization of lactose. The stirred solution was cooled to about 5° C. and below with the stirring continued for about 4 hours. When the lactose was crystallized to a satisfactory extent, it was separated with a decanter-type centrifuge. The resulting concentrated whey solution was decolored with a suitable amount of activated carbon and spray-dried to obtain 100 g of the titled compound in powder form. This whey concentrate had a mineral content of 60%.

EXAMPLES

1. Tablet type:

Nine parts of the whey concentrate (60% mineral content), 10 parts of sodium carbonate, 26 parts of sodium hydrogencarbonate, 30 parts of malic acid, 25 parts of sodium sulfate, a perfume (q.s.) and a dyestuff (q.s.) were mixed thoroughly with a stirrer. The resulting mixed powder was compressed with a tablet machine to make a bath preparation in tablets.

One tablet (5.0 g) was added to the bath water (200 liters) and its ability to warm the human body was evaluated by 30 panelists.

| Average increase in body temperature (°C.) | | |
|---|---|---|
| | Immediately after bathing | 30 Minutes after bathing |
| Treated bath water | 0.8 | 0.4 |
| Untreated bath water | 0.2 | 0 |

An investigation conducted 30 minutes after the bathing showed that all panelists felt warmer after bathing in the treated bath water than in the untreated bath water.

2. Powder type:

Twenty parts of the whey concentrate (50% mineral content), 80 parts of sodium sulfate, a perfume (q.s.) and a dyestuff (q.s.) were intimately mixed with a stirrer to make a bath preparation in powder form.

The ability of the powder to warm the human body was evaluated by 30 panelists as in Example 1. All panelists felt much warmer after bathing in the treated bath water than in the untreated bath water.

3. Solution type:

Sixty parts of the whey concentrate (40% mineral content), 10 parts of ethanol, 1 part of carboxymethyl cellulose sodium, a dyestuff (q.s.), a perfume (q.s.) and 29 parts of deionized water were mixed intimately and processed with a homomixer to make a bath preparation in solution form.

As in Example 1, the ability of the solution to warm the human body was evaluated by 30 panelists, who answered unanimously that they felt much warmer after bathing in the treated bath water than in the untreated bath water.

What is claimed is:

1. A bath preparation comprising a whey concentrate in an amount of 2-80 weight % and a mineral content of 40-70 weight % of said concentrate;
   wherein said whey concentrate is produced by using a permeate obtained by ultrafiltration, concentrating said permeate under vacuum to obtain a solid content of between about 40-60%, and removing crystallized lactose from said solids at low temperatures.

2. A bath preparation according to claim 1 which further contains a bubbling agent.

3. A bath preparation comprising a whey concentrate in an amount of 2-80 weight % and mineral content of 40-70 weight % of said concentrate;
   said whey concentrate is produced by using a permeate obtained by ultrafiltration, concentrate said permeate under vacuum to obtain a solid content of between about 40-60%, and removing crystallized lactose from said solids at low temperatures;
   wherein said whey concentrate is decolored with activated carbon and spray-dried to form a powder.

4. A bath preparation comprising a whey concentrate in an amount of 2-80 weight % and a mineral content of 40-70 weight % of said concentrate;
   said whey concentrate is produced by using a permeate obtained by ultrafiltration, concentrating said permeate under vacuum to obtain a solid content of between about 40-60%, and removing crystallized lactose from said solids at low temperatures;
   wherein said whey concentrate is in solution form and further contains ethanol, sodium carboxymethyl cellulose, dyestuff, a perfume and deionized water.

* * * * *